United States Patent
Golas et al.

(10) Patent No.: US 10,130,576 B2
(45) Date of Patent: Nov. 20, 2018

(54) ORAL CARE COMPOSITIONS

(71) Applicant: Johnson & Johnson Consumer Inc., Skillman, NJ (US)

(72) Inventors: Patricia L. Golas, New Brunswick, NJ (US); Carolyn J. Mordas, Ewing, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 17 days.

(21) Appl. No.: 14/795,122

(22) Filed: Jul. 9, 2015

(65) Prior Publication Data

US 2015/0306007 A1    Oct. 29, 2015

Related U.S. Application Data

(63) Continuation-in-part of application No. 13/675,436, filed on Nov. 13, 2012.

(51) Int. Cl.
| | |
|---|---|
| *A61K 8/55* | (2006.01) |
| *A61K 8/37* | (2006.01) |
| *A61K 8/90* | (2006.01) |
| *A61K 47/24* | (2006.01) |
| *A61K 8/34* | (2006.01) |
| *A61K 8/49* | (2006.01) |
| *A61Q 11/00* | (2006.01) |
| *A61K 8/92* | (2006.01) |
| *A61K 9/00* | (2006.01) |

(52) U.S. Cl.
CPC .............. *A61K 8/553* (2013.01); *A61K 8/347* (2013.01); *A61K 8/90* (2013.01); *A61K 8/922* (2013.01); *A61K 47/24* (2013.01); *A61Q 11/00* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 3,959,458 A | 5/1976 | Agricola et al. | |
| 4,051,234 A | 9/1977 | Gieske | |
| 5,190,747 A | 3/1993 | Sekiguchi | |
| 5,286,719 A * | 2/1994 | Fost ...................... | A01N 57/12 514/114 |
| 5,723,106 A * | 3/1998 | Buch ....................... | A61K 8/34 424/49 |
| 5,817,295 A * | 10/1998 | Chaudhari ............... | A61K 8/34 424/49 |
| 6,585,961 B1 * | 7/2003 | Stockel ................ | A61K 8/0291 424/49 |
| 7,084,104 B2 | 8/2006 | Martin | |
| 7,087,650 B2 | 8/2006 | Lennon | |
| 2004/0018954 A1 * | 1/2004 | Su .......................... | A61K 8/34 512/1 |
| 2005/0048005 A1 | 3/2005 | Stockel | |
| 2007/0190080 A1 * | 8/2007 | Friedman ............. | A61K 9/1075 424/400 |
| 2007/0243275 A1 * | 10/2007 | Gilbard ................ | A61K 9/0046 424/769 |
| 2008/0253976 A1 | 10/2008 | Scott et al. | |
| 2008/0287395 A1 * | 11/2008 | Ghosh ....................... | A61L 2/18 514/77 |
| 2011/0081433 A1 | 4/2011 | Kaur et al. | |
| 2011/0089073 A1 | 4/2011 | Baig | |
| 2011/0123462 A1 | 5/2011 | Mordas et al. | |
| 2012/0003162 A1 | 1/2012 | Mordas et al. | |
| 2012/0003163 A1 | 1/2012 | Mordas et al. | |
| 2012/0201902 A1 * | 8/2012 | Modak ................... | A01N 31/02 424/618 |

FOREIGN PATENT DOCUMENTS

| | | | | |
|---|---|---|---|---|
| DE | 102011084155 A1 * | 7/2012 | ............. | A61K 8/345 |
| WO | WO 2008042279 A2 | 4/2008 | | |
| WO | WO 2012/018519 A1 | 2/2012 | | |

OTHER PUBLICATIONS

Machine translation of DE 102011084155 A1.*
Wikipedia entry for "Coconut Oil" (downloaded May 5, 2017, from the site: https://en.wikipedia.org/wiki/Coconut_oil.*
C. F. Carson, K. A. Hammer, and T. V. Riley. Melaleuca alternifolia (Tea Tree) Oil: a Review of Antimicrobial and Other Medicinal Properties. Clinical Microbiology Reviews, Jan. 2006, p. 50-62 vol. 19, No. 1, p. 50-62.*
Cola®DetBSB Technical Data Sheet, supplied by Colonial Chemical. Downloaded Oct. 2, 2016, from the site: http://cosmetics.specialchem.com/product/i-colonial-chemical-cola-det-bsb.*
Machine translation of DE 102011084155 A1. Translation downloaded Oct. 2, 2016.*
Colalipid C technical data sheet from http://www.in-cosmetics.com/_novadocuments/241152?v=635997917797130000 Accessed Oct. 4, 2016.*
Hansch and Leo (cf., A. Leo, in Comprehensive Medicinal Chemistry, vol. 4, C. Hansch, P.G.Sammens, J.B. Taylor and C.A. Ramsden, Eds., p. 295, Pergamon Press, 1990).
UNIQEMA: "Further applications of biomimetic phospholipids," Research Disclosure, Mason Publications, Hampshire, GB, vol. 497, No. 9, Sep. 1, 2005 ISSN: 0374-4353.
Kabara, Jon J., Fatty Acids and Derivatives as Antimicrobial Agents, American Society for Microbiology, vol. 2., No. 1, Jul. 1972, pp. 23-28.
Croda, "Quaternaries" pamphlet, 2009, Croda Europe Ltd.
Business Briefing: Global Cosmetics Manufacturing 2004, "Phospholipids—A Natural Choice for Personal Care", pp. 1-6.
http://www.croda.com/home.aspx?view=list&d=content&s=157&r=401 &p=2578&productName=Arlasilk website: Croda.
Composition of coconut oil from Chempro, downloaded Sep. 8, 2014, from http://www.chempro.in/fattyacid.htm.
Datasheet for Arlasilk PTM from Croda, Inc. Downloaded on Sep. 8, 2014, from the site: http://www.ulprospector.com/en/na/PersonalCare/Detail/ 134/37143/Arlasilk—PTM.
Entry for Arlasilk PTC in Handbook of Green Chemicals, compiled by Michael and Irene Ash. Endicott, NY: Synapse Information Resources, 2004. p. 54 (partial).

\* cited by examiner

*Primary Examiner* — Michael P Cohen

(57) ABSTRACT

The present invention relates to oral compositions, comprising select phospholipid surfactants. Methods for using the compositions are also disclosed.

13 Claims, No Drawings

ORAL CARE COMPOSITIONS

CROSS-REFERENCE TO RELATED APPLICATION

This application is a continuation-in-part of pending U.S. application Ser. No. 13/675,436 filed on Nov. 13, 2012.

FIELD OF THE INVENTION

The present invention relates to oral compositions, comprising select phospholipid surfactants. Methods for using the compositions are also disclosed.

BACKGROUND OF THE INVENTION

The present invention relates to aqueous compositions suitable for use in oral hygiene, especially for cleaning the mouth and the teeth. In particular, the present invention is concerned with improved oral care compositions suitable for use as mouth washes, mouth rinses, dentifrices, toothpastes, gels, solutions or strips such as peroxide or non-peroxide tooth whitening strips and the like.

The damaging effect of certain surfactants used to solubilize product ingredients and/or cleanse the mucosae, particularly the mouth, has been the subject of intense study for many years in a search for "mild" products, which not only solubilize ingredients and cleanse efficiently, but also leave the mouth and teeth with a pleasant after feel, without irritation or other chemical damage to the gums or mucosae. We have now discovered quite unexpectedly, that by selection of specific phospholipid surfactants to modify the solubility characteristics of product formulations, compositions can be obtained which, in use, are capable of not only solubilizing water insoluble components such as water-insoluble antimicrobial agents, but maintaining or enhancing their bioavailability. Furthermore, the mildness of the composition is improved such that it can safely be used for cleansing the teeth and mucosae, including the gums when diseased or damaged. And, it is particularly useful for cleaning sensitive gums, for example when gingivitis is present.

SUMMARY OF THE INVENTION

It has been discovered that the aforementioned objective can be achieved by the compositions provided herein. In one embodiment, the present invention provides an oral composition comprising:
i. a phospholipid surfactant of formula I

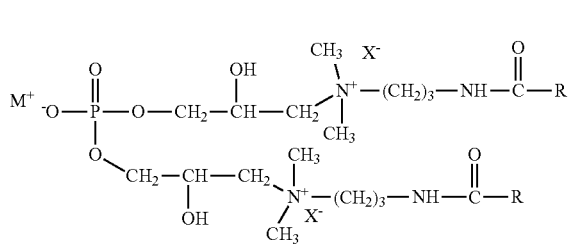

where $M^+$ is an alkali metal ion such as potassium or sodium;
$X^-$ is a halo; and
R is independently a straight or branched chain alkyl of (or containing) less than 17 carbons;
ii. one or more water-insoluble bioactive agents; and
iii. at least one orally acceptable solvent.

In further embodiments, the present invention relates to methods of treating plaque, gingivitis or gum disease, comprising the step of applying to the tissues (i.e., soft and hard) of the oral cavity of a mammal in need of such treatment the oral composition of the present invention in an amount effective to reduce or prevent tooth decay and/or reduce or prevent the symptoms associated with plaque, gingivitis or gum disease.

In still further embodiments, the present invention relates to methods of treating or reducing symptoms associated with inflamed tissue, comprising the step of applying to the tissues of a mammal in need of such treatment an amount of the composition of the present invention effective to reduce symptoms associated inflammation.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, solutions, mousse, foam, denture care product, mouth spray, lozenge or chewable tablet. The oral care composition may also be incorporated onto floss, strips or films for direct application or attachment to oral surfaces or integrated into a device or applicator such as a toothbrush or roll-ons. Such applicators may be for single or multiple use.

The phrase "reduced level" of alcohol means an amount of a C2-C4 monohydric alcohol up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total composition. Optionally, the compositions of the present invention are free of C2-C4 monohydric alcohols.

The term "halo" means an element of the halogen family. Preferred halo moieties include fluorine, chlorine, bromine or iodine.

Unless otherwise specified, the phrase "oil(s) or "oily component(s)" means any hydrophobic, water immiscible compound.

The terms "hydrophobic", "hydrophobicity" or "degree of hydrophobicity" of an oil or oily component of the present invention or any mixture of such oil or oily components is represented by the Octanol Water Partition Coefficient ($K_{ow}$). $K_{ow}$ is the ratio of the concentration by weight of an oil or oily component in the octanol phase and the concentration by weight of the oil or oily component in water phase at equilibrium and at a specified temperature for the biphasic octanol and water system. The logarithm of $K_{ow}$ is called the log P. The experimental values used to calculate the $K_{ow}$ are typically measured at a temperature of between 20° C. to 25° C.

Alternatively, the log P values are conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each oil or oily component, and takes into account the numbers and types of atoms, the atom connectivity, and chemical bonding. The C log P values, which is considered reliable and a widely used estimate for this physicochemical property, can be used instead of the experimental $K_{ow}$ method for measuring log P values.

The higher the log P of the oil or oily component, the more hydrophobic (or, the greater the degree of hydrophobicity of) the oil or oily component.

All percentages, parts and ratios are based upon the total weight of the composition of the present invention, unless otherwise specified. All such weights as they pertain to the listed ingredients are based on the level of the particular ingredient described and, therefore, do not include carriers or by-products that may be included in commercially available materials, unless otherwise specified.

The compositions of the present invention may be in the form of mouth washes, mouth rinses, dentifrices, toothpastes, gels, solutions or strips such as non-peroxide tooth whitening strips and the like.

Phospholipid Surfactant

The compositions of the present invention comprise a phospholipid surfactant of formula I:

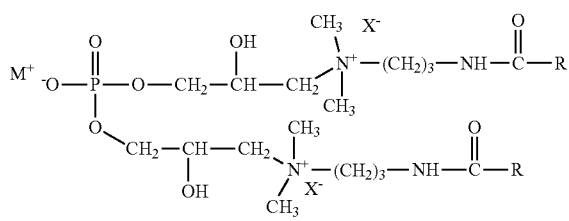

where $M^+$ is an alkali metal ion such as potassium or sodium;
$X^-$ is a halo; and
R is independently a straight or branched chain alkyl of less than 17 carbons, optionally a ($C_1$ to $C_{15}$)-alkyl, optionally a ($C_5$ to $C_{15}$)-alkyl, optionally a ($C_7$ to $C_{15}$)-alkyl, optionally a ($C_9$ to $C_{15}$)-alkyl, or optionally ($C_9$ to $C_{13}$)-alkyl;
wherein the phospholipid surfactant has a degree of unsaturation of less than 1 or, optionally, zero. In certain embodiments, R is a straight chain alkyl of less than 17 carbons.

Examples of suitable phospholipid surfactants include, but are not limited to cocamidopropyl PG-dimonium chloride phosphate; myristamidopropyl PG-dimonium chloride phosphate; lauramidopropyl PG-dimonium chloride phosphate and mixtures thereof. In certain embodiments, the phospholipid surfactant is selected from the group consisting of cocamidopropyl PG-dimonium chloride phosphate; myristamidopropyl PG-dimonium chloride phosphate and mixtures thereof. In certain embodiments the phospholipid surfactant is myristamidopropyl PG-dimonium chloride phosphate.

The phospholipid surfactant can be present at concentrations of from 0.01% (or about 0.01%) to 10% (or about 10%), optionally 0.1% (or about 0.1%) to 3% (or about 3%), or optionally from 0.5% (or about 0.5%) to 1.5% (or about 1.5%).

Water-Insoluble Noncationic Bioactive Agents

The compositions of the present invention also comprise a water-insoluble noncationic bioactive agent. Typical examples of such agents, useful when considering anticaries, antiplaque, antigingivitis or gum disease treatment (or symptom reduction) effectiveness, safety and formulation, are:

I. Antimicrobial water-insoluble noncationic bioactive agents such as:
Halogenated Diphenyl Ethers
2',4,4'-trichloro-2-hydroxy-diphenyl ether (Triclosan)
2,2'-dihydroxy-5,5'-dibromo-diphenyl ether.
Halogenated Salicylanilides
4'5-dibromosalicylanilide
3,4',5-trichlorosalcylanilide
3,4',5-tribromosalicylanilide
2,3,3',5-tetrachlorosalicylanilide
3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Flurophene).
Benzoic Esters
Methyl-p-Hydroxybenzoic Ester
Ethyl-p-Hydroxybenzoic Ester
Propyl-p-Hydroxybenzoic Ester
Butyl-p-Hydroxybenzoic Ester.
Halogenated Carbanilides
3,4,4'-trichlorocarbanilide
3-trifluoromethyl-4,4'-dichlorocarbanilide
3,3',4-trichlorocarbanilide.
Phenolic Compounds (including phenol and its homologs, mono- and poly-alkyl and aromatic halo (e.g. F, Cl, Br, I)-phenols, resorcinol and catechol and their derivatives and bisphenolic compounds). Such phenolic compounds includes inter alia:
Phenol and its Homologs
Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n-Propyl-Phenol
4-n-Butyl-Phenol 4-n-Amyl-Phenol
4-tert-Amyl-Phenol
4-n-Hexyl-Phenol
4-n-Heptyl-Phenol
2-Methoxy-4-(2-Propenyl)-Phenol (Eugenol)
Mono- and Poly-Alkyl and Aralkyl Halophenols
Methyl-p-Chlorophenol
Ethyl-p-Chlorophenol
n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol
O-Chlorophenol
Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-Chlorophenol
n-Heptyl-o-Chlorophenol
p-Chlorophenol
o-Benzyl-p-Chlorophenol
o-Benzyl-m-methyl-p-Chlorophenol
o-Benzyl-m,m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-Propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-chloro-2-methyl phenol
4-chloro-3-methyl phenol
4-chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-chloro-2-hydroxydiphenylemthane.

Resorcinol and its Derivatives
Resorcinol
Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane.
Bisphenolic Compounds
Bisphenol A
2,2'-methylene bis(4-chlorophenol)
2,2'-methylene bis(3,4,6-trichlorophenol) (hexachlorophene)
2,2'-methylene bis(4-chloro-6-bromophenol)
bis(2-hydroxy-3,5-dichlorophenyl) sulfide
bis(2-hydroxy-5-chlorobenzyl) sulfide.

Other antimicrobial water-insoluble noncationic bioactive agents include, but are not limited to: fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid and mixtures thereof; long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof);

Also useful as antimicrobial water-insoluble noncationic bioactive agents are one or more bioactive essential oils. Nonlimiting examples of such essential oils include:

Thymol, [$(CH_3)_2CHC_6H_3(CH_3)OH$, also known as isopropyl-m-cresol], is only slightly soluble in water but is soluble in alcohol;

Methyl salicylate, [$C_6H_4OHCOOCH_3$, also known as wintergreen oil], additionally provides flavoring together with its antimicrobial function;

Eucalyptol ($C_{10}H_{18}O$, also known as cineol) is a terpene ether and provides a cooling, spicy taste. Eucalyptol may be used in place of thymol in certain formulations in the same amount if desired; and Menthol ($CH_3C_6H_9(C_3H_7)OH$, also known as hexahydrothymol) is also only slightly soluble in alcohol, and is fairly volatile. Menthol, in addition to any antiseptic properties, provides a cooling, tingling sensation.

II. Anti-inflammatory and/or analgesic water-insoluble noncationic bioactive agents such as:

NFkB-inhibitor such as substituted resorcinols (such as 4-hexyl resorcinol and 4-octylresorcinol), (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts of *Paulownia tomentosa* wood, and combinations thereof; *phellodendron amurense* cortex extract (PCE), feverfew (*Tanacetum parthenium*), ginger (*Zingiber officinale*), ginko (*Ginko Biloba*), cotinus (*Cotinus coggygria*), goji berry (*Lycium barbarum*), milk thistle extract (*Silybum marianum*), honeysuckle (*Lonicera japonica*), basalm of Peru (*Myroxylon pereirae*), sage (*Salvia officinalis*), cranberry extract (*Vaccinium oxycoccos*), amaranth oil (*Amaranthus cruentus*), pomegranate (*Punica granatum*), yerbe mate (*Ilex paraguariensis* Leaf Extract), white lily flower extract (*Lilium Candidum*), olive leaf extract (*Olea europaea*), phloretin (apple extract), lifenol (hops: *Humulus lupulus*) extract, licochalcone (licorice: *Glycyrrhiza inflate* extract ingredient), symrelief (bisabolol and ginger extract), Magnolol (extract from bark of the *Houpu magnolia* [*Magnolia officinalis*], Honokiol (extract from cones, bark, and leaves of *Magnolia grandifloris*] and mixtures thereof; non-steroidal anti-inflammatory agents such as salicylic acid derivatives (e.g. aspirin), paraminophenol derivative (e.g. acetaminophen), indole and indene acetic acids (indomethacin, sulindac and etodalac), heteroaryl acetic acids (tolmetin diclofenac and ketorolac), aryl propionic acid derivatives (ibuprofen, naproxen, ketoprofen, fenopren, oxaprozine), anthranilic acids (mefenamic acid, meclofenamic acid), enolic acids (piroxicam, tenoxicam, phenylbutazone and oxyphenthatrazone) and mixtures thereof.

Other useful water-insoluble noncationic bioactive agents can be found in US Patent Publication 2007/0190080 to Doron Friedman, herein incorporated by reference in its entirety.

The water-insoluble, noncationic bioactive agent is present in the oral composition in an amount effective to achieve biologic activity such as anti-inflammation, analgesic, anti-caries, antiplaque, antigingivitis or reduction in the symptoms of gum disease. The antimicrobial effective amount of the water-insoluble, noncationic bioactive agent ranges from about 0.01%, optionally from about 0.01% to about 5%, optionally from about 0.03% to about 1%, or optionally from about 0.03% to about 0.5%, by weight of the total composition. The noncationic bioactive agent is water-insoluble, or substantially water-insoluble, meaning that its solubility is less than about 1%, optionally less than about 0.5%, or optionally less than about 0.1%, by weight in water at 25° C.

In certain embodiments, the bioactive essential oils are used in amounts effective to provide antimicrobial activity in the oral cavity. In certain embodiments, the bioactive essential oils are used in amounts effective to provide analgesic or anti-inflammatory activity in the oral cavity. In specific embodiments, the total amount of bioactive essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contains a bioactive essential oil selected from the group consisting of thymol, eucalyptol, menthol, methyl salicylate, or/and mixtures thereof. In certain embodiments, the composition contains all four of these bioactive essential oils.

In certain embodiments, thymol is employed in amounts of from 0.001% (or about 0.001%) to 0.25% (or about 0.25%) w/v, or optionally from 0.04% (or about 0.04%) to 0.07% (or about 0.07%) w/v of the composition. In certain embodiments, eucalyptol may be employed in amounts of from 0.001% (or about 0.001%) to 0.11% (or about 0.11%) w/v, or optionally from 0.085% (or about 0.085%) to 0.10% (or about 0.10%) w/v of the composition. In certain embodiments, menthol is employed in amounts of from 0.001% (or about 0.001%) to 0.25% (or about 0.25%) w/v, or optionally from 0.035% (or about 0.035%) to 0.05% (or about 0.05%) w/v of the composition. In certain embodiments, methyl salicylate is employed in amounts of from 0.001% (or about 0.001%) to 0.08% (or about 0.08%) w/v, or optionally from 0.04% (or about 0.04%) to 0.07% (or about 0.07%) w/v of the composition.

Orally Acceptable Solvent

The compositions of the present invention further comprise an orally acceptable solvent. Orally acceptable solvents include, but are not limited to, water, $C_2$-$C_4$ monohydric alcohols, propylene glycol, and mixtures thereof. When present, the $C_2$-$C_4$ monohydric alcohols are at a reduced level.

Optional Components

The antimicrobial properties of the present invention can be illustrated by use of log RLU (relative light units) data. A decreasing log RLU, relative to a negative control (typically sterile water), reflects a corresponding decrease in the number of viable bacteria present in measurement system. In certain embodiments, the compositions of the present invention exhibit reductions in log RLU values (versus a negative control) at least 0.5 (or about 0.5), optionally 1.0 (or about 1.0) optionally, 2.0 (or about 2.0), or optionally 3.0 (or about 3.0).

In certain embodiments, the compositions of the present invention exhibit a high level of antimicrobial activity as measured by an M-factor greater than 0.5 (or about 0.5), optionally 1.0 (or about 1.0) optionally, 2.0 (or about 2.0), or optionally 3.0 (or about 3.0) where "M-factor" equals the log RLU (relative light units) value of water used as the negative control minus the log RLU value of the mouth rinse composition being tested. In addition, the oral mouth rinse compositions of this invention are clear (to the unaided human eye) and aesthetically appealing products.

The compositions of the present invention may further comprise optional components (collectively referred to as orally acceptable carriers or excipients) which are described in the following paragraphs along with non-limiting examples. These orally acceptable carrier materials include one or more compatible solid or liquid excipients or diluents which are suitable for topical oral administration. By "compatible" is meant that the components of the composition are capable of being commingled without interaction in a manner which would substantially reduce composition stability and/or efficacy. Suitable carriers or excipients are well known in the art. Their selection will depend on secondary considerations like taste, cost, and shelf stability, etc. Although a general list of optional components is provided below, a more detailed discussion of suitable optional components (including excipients and carriers) can be found in US Patent Publication 20110089073 to Baig et al., herein incorporated by reference in its entirety.

The Solvent System

In certain embodiments, the mouth rinse compositions of the present invention also include a solvent system comprising at least one polyol solvent and at least one sugar alcohol.

Polyol Solvent

Polyol or polyhydric alcohol solvents suitable for use in the solvent system of the present invention includes polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 1.0% (or about 1.0%) to 30.0% (or about 30.0%) w/v, or optionally from 3.0% (or about 3.0%) to 15.0% (or about 15.0%) w/v of the composition.

Sugar Alcohol Solvent

The sugar alcohol solvent(s) may be selected from those multi-hydroxy-functional compounds that are conventionally used in oral and ingestible products. In certain embodiments, the sugar alcohol (s) should be non-metabolized and non-fermentable sugar alcohol (s). In specific embodiments, the sugar alcohols include, but are not limited to xylitol, sorbitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. Optionally, the sugar alcohol is sorbitol.

In certain embodiments, the total amount of sugar alcohol (s) which are added to effectively aid in the dispersion or dissolution of the active ingredients should not exceed 30% w/v (or about 30% w/v) of the composition. Optionally, total amount of sugar alcohol should not exceed 20% w/v (or about 20% w/v) of the composition. The sugar alcohol can be in an amount of from 1.0% (or about 1.0%) to 30.0% (or about 30.0%) w/v, or optionally from 10.0% (or about 10.0%) to 20.0% (or about 20.0%) w/v of the composition.

In certain embodiments, the total amount of the solvent system which is added to effectively aid in the dissolution or dispersion of the active ingredients should not exceed 60% w/v (or about 60% w/v) of the composition. Optionally, total amount of solvent system should not exceed 25% w/v (or about 25% w/v) of the composition. The solvent system can be in an amount of from 2% (or about 2%) to 60% (or about 60%) w/v, or optionally from 10% (or about 10%) to 20% (or about 20%) w/v of the composition.

In certain embodiments, the ratio of the sugar alcohol to the polyol solvent in the composition should be from 10:1 (or about 10:1) to 1:10 (or about 1:10), optionally from 5:1 (or about 5:1) to 1:5 (or about 1:5), optionally 1:3 (or about 1:3) by weight.

Additional Surfactant

In certain embodiments, the present invention contains a surfactant in addition to the phospholipid surfactants of formula I to aid in solubilization of essential oils if present, provided such additional surfactants do not affect the bioavailability of the essential oils. Suitable examples include anionic surfactants, nonionic surfactants, amphoteric surfactants and mixtures thereof.

Anionic surfactants useful herein include, but are not limited to, sarcosine type surfactants or sarcosinates; taurates such as sodium methyl cocoyl taurate; alkyl sulfates such as sodium trideceth sulfate or sodium lauryl sulfate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; ethoxylated hydrogenated castor oils available commercially for example under the trade name CRODURET (Croda Inc., Edison, N.J.), and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof. Also useful as nonionic surfactants are poly(oxyethylene)-poly(oxypropylene) block copolymers. Such copolymers are known commercially as poloxamers and are produced in a wide range of structures and molecular weights with varying contents of ethylene oxide and propylene oxide. The nonionic poloxamers according to the invention are non-toxic and acceptable as direct food additives. They are stable and readily dispersible in aqueous systems and are compatible with a wide variety of formulating ingredients for oral preparations. These surfactants should have an HLB (Hydrophilic-Lipophilic Balance) of between about 10 and 30 and preferably between 10 and 25.

Thus, non-ionic surfactants useful in this invention include, but are not limited to the following poloxamers:

105 188 237 334
108 215 238 335
124 217 284 338
184 234 288 407
185 235 333

Generally these poly(oxyethylene)-poly(oxypropylene) block copolymers should constitute from about 0.04% w/v to about 6.0% w/v by weight of total volume of composition (% w/v) and optionally from 0.1% to 0.3% w/v. Another useful class of nonionic surfactants are polyoxyethylene sorbitan fatty acid esters, e.g., materials sold under the trademark Tween. Examples of such materials are polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), polyoxyethylene (5) sorbitan monooleate (Tween 81), and polyoxyethlene (20) sorbitan trioleate (Tween 85), and mixtures thereof. When present, the polyoxyethylene sorbitan fatty acid esters are present at a concentration of from about 0.04% w/v to about 6.0% w/v, optionally from about 0.2% w/v to about 0.8% w/v.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the additional surfactant is a poly(oxyethylene)-poly(oxypropylene) block copolymers surfactant. In certain embodiments, the poly(oxyethylene)-poly(oxypropylene) block copolymer surfactant is poloxamer 407 having an HLB of about 22. Such polymers are sold under the trademark Pluronic F-127® (BASF-WYANDOTTE).

Other Optional Components

The compositions of the present invention may also include one or more optional ingredients nonexclusively including a thickening agent, additional humectants, chelating agents, whitening agents, and additives such as flavorants, preservatives, pH adjusting agents, and the like. The pH of the compositions of this invention is optionally maintained at range of below 5 (or about 5), optionally, below 4.5 (or about 4.5) or, optionally, in the range of from 4.4 (or about 4.4) to 3 (or about 3), or optionally in the range of from 3.5 (or about 3.5) to 4.2 (or about 4.2).

Commercially available thickening agents, which are capable of imparting the appropriate viscosity to the compositions, are suitable for use in this invention. Examples of suitable thickening agents nonexclusively include: mono or diesters of 1) polyethylene glycol of formula: HO—$(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the trade name, "PEG 6000 DS".

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name, "Versene 100XL" and is present in an amount, based upon the total weight of the composition, from about 0 to about 0.5 percent, and preferably from about 0.05 percent to about 0.25 percent.

Suitable preservatives include, sodium benzoate, and polysorbate and are present in the composition in an amount, based upon the total weight of the composition, from about 0 to about 0.2 percent, and preferably from about 0.05 percent to about 0.10 percent.

In certain embodiments, the compositions of the present invention are free of or essentially free of bioavailability affecting compounds. As used herein, "bioavailability affecting compound", means compounds that negatively affect the bioavailability of any incorporated essential oils such as by binding the essential oils or otherwise inactivating the essential oils. "Essentially free" as used with respect to bioavailability affecting compounds is defined as formulations having less than 5% (or about 5%), optionally, 3% (or about 3%), optionally, 1% (or about 1%), or optionally 0.1, or optionally, 0.01% (or about 0.01%), by weight (w/v) of the total composition of a bioavailability affecting compound. In certain embodiments, the bioavailability affecting compound can include, but is not limited to, polyethylene oxide/polypropylene oxide block copolymers such as poloxamers; cyclodextrins; polysorbates such as Tweens; and mixtures thereof. Additionally or alternatively, the bioavailability affecting compound can include any oil or oily component where the oil or oily component is an oil or oily component or a mixture of oils or oily components such that the hydrophobicity (or degree of hydrophobicity) of the oil or oily component is less than the hydrophobicity (or degree of hydrophobicity) of the water-insoluble noncationic bioactive agents. In certain embodiments, the oil or oily component has a log P of no more than or less than 2.1 (or about 2.1), optionally 2.0 (or about 2.0). In certain embodiments, the bioavailability affecting oil or oily component is or comprises at least one organic acid. Such organic acids include, but are not limited to, ascorbic acid, sorbic acid, citric acid, glycolic acid, lactic acid and acetic acid, benzoic acid, salicylic acid, phthalic acid, phenolsulphonic acid, succinic acid and mixtures thereof, optionally, the organic acid is selected from the group consisting of benzoic acid, sorbic acid, succinic acid, citric acid and mixtures thereof, or optionally, the organic acid is benzoic acid.

If incorporated into the compositions of the present invention, to minimize its bioavailability affecting properties, the oil or oily component can be incorporated in the form of a premix as disclosed in US Patent Publication 2012/0003162 to Mordas et al., which publication is herein incorporated by reference in its entirety.

The above described compositions may be prepared by combining the desired components in a suitable container and mixing them under ambient conditions in any conventional mixing means well known in the art, such as a mechanically stirred propeller, paddle, and the like. The order of mixing is not critical.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

The following examples are illustrative only and should not be construed as limiting the invention in any way. Those skilled in the art will appreciate that variations are possible which are within the spirit and scope of the appended claims.

Example I

Single Species Biofilm Assay Experiment I

Seven essential oil based mouth rinse formulations are prepared (i.e., formulation Examples A through G of Table 1) incorporating various phospholipid surfactants that are approved for use in oral care products and tested using an in-vitro single species S. mutans biofilm model. A 24-hour S.

*mutans* biofilm is grown on a polystyrene peg plate (96 pegs, N=6 per test group). The pegs were subsequently treated for thirty seconds with each of formulations A through G, as well as positive and negative controls. The treatment is applied as a single thirty (30) second treatment. The positive control is a commercially available essential oil mouth rinse. The negative control is sterile water.

After treatment the biofilm is neutralized and rinsed. The biofilm is harvested via sonication using a Misonix Ultrasonic Liquid Processor (Farmingdale, N.Y.). Using a Celsis Rapid Detection RapiScreen kit (Celsis International PLC, Chicago), the bacteria are lysed with Celsis Luminex and then the adenosine triphosphate (ATP) from the lysed bacteria is measured using the bioluminescence marker LB960 Microplate Luminometer supplied by Berthold (Wildbad, Germany). Data are reported in log RLU (relative light units) where decreasing log RLUs indicates fewer viable bacteria remaining on the biofilm substrate.

The eight formulations as well as results of the *S. mutans* biofilm kill tests, in log RLU units, are shown on Table 1. The log RLU for sterile water (negative control) is 7.69 and the log RLU for the commercially available essential oil mouthrinse (positive control) is 5.98. Final formulations are determined to be about pH 4.2 (±0.1). The formulations of Table 1 are prepared using conventional mixing technology. The letters in parentheses next to M-factor values indicate statistical significance. Formulas that share a letter are not statistically significantly different.

TABLE 1

| Ingredients | Example A (% w/w) | Example B (% w/w) | Example C (% w/w) | Comparative Example D (% w/w) | Comparative Example E (% w/w) |
|---|---|---|---|---|---|
| Menthol | 0.042 | 0.042 | 0.042 | 0.042 | 0.042 |
| Methyl salicylate | 0.065 | 0.065 | 0.065 | 0.065 | 0.065 |
| Thymol | 0.062 | 0.062 | 0.062 | 0.062 | 0.062 |
| Eucalyptol | 0.090 | 0.090 | 0.090 | 0.090 | 0.090 |
| Poloxamer 407 | — | — | — | — | — |
| Arlasilk PTM[1] | 0.60 | — | — | — | — |
| ColaLipid C[2] | — | 0.85 | — | — | — |
| ColaLipid M[3] | — | — | 0.9 | — | — |
| ColaLipid SAFL[4] | — | — | — | 0.82 | — |
| ColaLipid BP[5] | — | — | — | — | 0.75 |
| Arlasilk CDM[6] | — | — | — | — | — |
| ColaLipid SUN[7] | — | — | — | — | — |
| Sorbitol (70% solution) | 19.63 | 19.63 | 19.63 | 19.63 | 19.63 |
| Ethanol | 18.2 | 18.2 | 18.2 | 18.2 | 18.2 |
| Benzoic Acid | 0.12 | 0.12 | 0.12 | 0.12 | 0.12 |
| Sodium Benzoate | 0.035 | 0.035 | 0.035 | 0.035 | 0.035 |
| Flavor | 0.083 | 0.083 | 0.083 | 0.083 | 0.083 |
| Sweetener | 0.11 | 0.11 | 0.11 | 0.11 | 0.11 |
| Color | 0.0005 | 0.0005 | 0.0005 | 0.0005 | 0.0005 |
| Water | QS | QS | QS | QS | QS |
| TOTAL | 100.0 | 100.0 | 100.0 | 100.0 | 100.0 |
| log RLU | 5.45 | 5.46 | 5.58 | 5.91 | 5.93 |
| M-factor | 2.24 (a) | 2.23 (ab) | 2.11 (abc) | 1.78 (cd) | 1.76 (cde) |

| Ingredients | Comparative Example F (% w/w) | Comparative Example G (% w/w) | Positive Control (% w/w) | Negative Control |
|---|---|---|---|---|
| Menthol | 0.042 | 0.042 | 0.042 | — |
| Methyl salicylate | 0.065 | 0.065 | 0.065 | — |
| Thymol | 0.062 | 0.062 | 0.062 | — |
| Eucalyptol | 0.090 | 0.092 | 0.092 | — |
| Poloxamer 407 | — | — | 0.25 | — |
| Arlasilk PTM[1] | — | — | — | — |
| ColaLipid C[2] | — | — | — | — |
| ColaLipid M[3] | — | — | — | — |
| ColaLipid SAFL[4] | — | — | — | — |
| ColaLipid BP[5] | — | — | — | — |
| Arlasilk CDM[6] | 2.05 | — | — | — |
| ColaLipid SUN[7] | — | 1.35 | — | — |
| Sorbitol (70% solution) | 19.63 | 19.63 | 19.63 | — |
| Ethanol | 18.2 | 18.2 | 18.2 | — |
| Benzoic Acid | 0.12 | 0.12 | 0.12 | — |
| Sodium Benzoate | 0.035 | 0.035 | 0.035 | — |
| Flavor | 0.083 | 0.083 | 0.083 | — |
| Sweetener | 0.11 | 0.11 | 0.11 | — |

TABLE 1-continued

| | | | | |
|---|---|---|---|---|
| Color | 0.0005 | 0.0005 | 0.0005 | — |
| Water | QS | QS | QS | — |
| TOTAL | 100.0 | 100.0 | 100.0 | — |
| log RLU | 6.04 | 6.23 | 5.98 | 7.69 |
| M-factor | 1.65 (def) | 1.46 (defg) | 1.95 (defg) | 0 |

[1]Myristamidopropyl PG-dimonium chloride phosphate, 40% in water (Croda Inc., Edison, NJ)
[2]Cocamidopropyl PG-dimonium chloride phosphate, 41% in water (Colonial Chemical, Inc., South Pittsburg, TN)
[3]Myristamidopropyl PG-dimonium chloride phosphate, 39% in water (Colonial Chemical, Inc., South Pittsburg, TN)
[4]Linoleamidopropyl PG-dimonium chloride phosphate, 29% in water (Colonial Chemical, Inc., South Pittsburg, TN)
[5]Sodium borageamidopropyl PG-dimonium chloride phosphate, 35% in water (Colonial Chemical, Inc., South Pittsburg, TN)
[6]Sodium coco PG-dimonium chloride phosphate, 31% in water (Croda Inc., Edison, NJ)
[7]Sodium sunflowerseedamidopropyl PG-dimonium chloride phosphate, 31% in water (Colonial Chemical, Inc., South Pittsburg, TN)

Table 1 shows biocidal activity (in the form of M-factor values) ranging from 1.46 to 2.24 (log RLU values 5.45 to 6.23), depending on the presence and identity of phospholipid surfactant. Specifically, phospholipid surfactants where R (as in formula I) is an alkyl of less than 17 carbons display the highest activity, which is evaluated based on statistically significant difference from the positive control. Examples A, B, and C show M-factor values that are statistically significantly lower (more efficacious) than the positive control, whereas Comparative Examples D, E, F, and G show M-factor values that are statistically equivalent to the positive control.

Example II

Assessing Presence of Solvent System and Tween Surfactants

Two essential oil based mouth rinse formulations are prepared (i.e., formulation Examples H and I of Table 2) incorporating the phospholipid surfactant as sold under the brand name Arlasilk PTC, but adding no polyol/sugar alcohol solvent system. Only Example I contained Tween 20.

The two formulations are tested using an in-vitro single species S. mutans biofilm model. A 24-hour S. mutans biofilm is grown on a polystyrene peg plate (96 pegs, N=6 per test group). The pegs were subsequently treated for thirty seconds with each of formulations H and I, as well as positive and negative controls. The treatment is applied as a single thirty (30) second treatment. The positive control is a commercially available essential oil mouth rinse. The negative control is sterile water.

After treatment the biofilm is neutralized and rinsed. The biofilm is harvested via sonication using a Misonix Ultrasonic Liquid Processor (Farmingdale, N.Y.). Using a Celsis Rapid Detection RapiScreen kit (Celsis International PLC, Chicago), the bacteria are lysed with Celsis Luminex and then the adenosine triphosphate (ATP) from the lysed bacteria is measured using the bioluminescence marker LB960 Microplate Luminometer supplied by Berthold (Wildbad, Germany). Data are reported in log RLU (relative light units) where decreasing log RLUs indicates fewer viable bacteria remaining on the biofilm substrate.

The two formulations as well as results of the S. mutans biofilm kill tests, in log RLU units, are shown on Table 2. A log RLU value of 7.56+/−0.09 (95% confidence interval) is used as the negative control representing the average log RLU of sterile water. This average was determined by evaluating the log RLU of 52 different sterile water samples using the method described in this example. Similarly, a log RLU value of 5.48+/−0.11 (95% confidence interval) is used as the positive control representing the average log RLU for the samples having the formula exemplified under the essential oil (EO) formulation in Table 2. This average log RLU was determined by evaluating the log RLU of 66 different samples having the formula exemplified under the EO formulation in Table 2, using the method described in this example.

Final formulations of Table 2, including the various EO formulation samples used to establish the average log RLU for the positive control, are adjusted to about pH 4.2 (±0.1) with 1M HCl or NaOH as needed. The formulations of Table 2 are prepared using conventional mixing technology.

TABLE 2

| Ingredients | Example H (% w/w) | Example I (% w/w) | EO Formulation Establishing Ave. log RLU for Positive Control (% w/w) | Negative Control |
|---|---|---|---|---|
| Propylene glycol | 10.0 | 10.0 | — | — |
| Arlasilk PTC[1] | 2.0 | 2.0 | — | — |
| Benzoic Acid | 0.30 | 0.30 | 0.035 | — |
| Menthol | 0.042 | 0.042 | 0.042 | — |
| Methyl salicylate | 0.060 | 0.060 | 0.065 | — |
| Thymol | 0.064 | 0.064 | 0.062 | — |
| Eucalyptol | 0.092 | 0.092 | 0.092 | — |
| Tween 20 | — | 2.00 | — | — |
| Poloxamer 407 | — | — | 0.25 | — |
| Ethanol | — | — | 18.2 | — |
| Sorbitol (70% solution) | — | — | 19.3 | — |
| Sodium Benzoate | 0.30 | 0.30 | 0.12 | — |
| Flavor | — | — | 0.083 | — |
| Sweetener | — | — | 0.11 | — |
| Color | — | — | 0.0005 | — |
| Water | 87.1 | 85.1 | QS | — |
| TOTAL | 100.0 | 100.0 | — | — |
| log RLU | 6.06 | 7.75 | 5.48* | 7.56** |

[1]Cocamidopropyl PG-dimonium chloride phosphate, 47% in water (Croda, South Pittsburg, TN)
*Ave. log RLU value of 66 different samples, each having the formula of the listed EO formulation
**Ave. log RLU value of 52 different sterile water samples Table 2 shows that formulations containing the phospholipid surfactant, but free of the optional polyol/sugar alcohol solvent system, exhibit decreased biocidal activity in the presence of Tween 20, indicating a lower biocidal activity for Tween 20 containing Example I (log RLU=7.75) versus the higher biocidal activity of "Tween" free Example H (log RLU=6.06).

Example III

Multi Treatment Static Biofilm Assay Method

Additionally, non-ethanol containing formulations of the present invention (i.e., Examples J through Q of Table 3) are tested using a multi treatment static biofilm assay method. The formulations are prepared using conventional mixing technology. The final formulations are determined to be about pH 4.2 (±0.1). A 24-hour salivary biofilm is grown on a polystyrene peg plate (96 pegs, N=16 per test group). The pegs are subsequently treated for thirty seconds with each of formulations J through Q, as well as positive and negative controls. The treatments are applied twice daily for a total of five treatments. The positive control is a commercially available essential oil mouth rinse. The negative control is sterile water.

After treatment the biofilm is neutralized and rinsed. The biofilm is harvested via sonication using a Misonix Ultrasonic Liquid Processor (Farmingdale, N.Y.). Using a Celsis Rapid Detection RapiScreen kit (Celsis International PLC, Chicago), the bacteria are lysed with Celsis Luminex and then the adenosine triphosphate (ATP) from the lysed bacteria is measured using the bioluminescence marker LB960 Microplate Luminometer supplied by Berthold (Wildbad, Germany). Data are reported in log RLU (relative light units) where decreasing log RLUs indicates fewer viable bacteria remaining on the biofilm substrate.

TABLE 3

| Raw material | Example J (% w/w) | Example K (% w/w) | Example L (% w/w) | Example M (% w/w) | Example N (% w/w) |
|---|---|---|---|---|---|
| Propylene glycol | 5.0 | 5.0 | 7.0 | 5.0 | 5.0 |
| Benzoic Acid | 0.086 | 0.086 | 0.086 | 0.086 | 0.086 |
| Menthol | 0.042 | 0.042 | 0.042 | 0.042 | 0.042 |
| Methyl salicylate | 0.064 | 0.064 | 0.064 | 0.064 | 0.064 |
| Thymol | 0.062 | 0.062 | 0.062 | 0.062 | 0.062 |
| Eucalyptol | 0.089 | 0.089 | 0.089 | 0.089 | 0.089 |
| Poloxamer 407 | 0.20 | 0.0 | 0.0 | 0.20 | — |
| Arlasilk PTM[1] | 0.20 | 1.05 | 1.05 | — | — |
| ColaLipid C[2] | — | — | — | 0.20 | 2.0 |
| Cocamidopropyl betaine | | | | | |
| Tween 20 | — | — | — | — | — |
| Sorbitol (70% solution) | 20.0 | 20.0 | 10.0 | 20.0 | 20.0 |
| Sodium Benzoate | 0.077 | 0.077 | 0.077 | 0.077 | 0.077 |
| Flavor | 0.017 | 0.017 | 0.017 | 0.017 | 0.017 |
| Sweetener | 0.0706 | 0.0706 | 0.0706 | 0.0706 | 0.0706 |
| FD&C Green #3 | 0.00004 | 0.00004 | 0.00004 | 0.00004 | 0.00004 |
| Water | QS | QS | QS | QS | QS |
| TOTAL | 100.0 | 100.0 | 100.0 | 100.0 | 100.0 |
| log RLU | 3.93 | 3.91 | 3.87 | 4.25 | 3.95 |
| M-factor | 3.29 | 3.31 | 3.35 | 2.97 | 3.27 |

| Raw material | Example O (% w/w) | Comparative Example P (% w/w) | Comparative Example Q (% w/w) | Positive Control (% w/w) | Negative Control |
|---|---|---|---|---|---|
| Propylene glycol | 7.0 | 7.0 | 7.0 | 7.0 | — |
| Benzoic Acid | 0.086 | 0.086 | 0.086 | 0.086 | — |
| Menthol | 0.042 | 0.042 | 0.042 | 0.042 | — |
| Methyl salicylate | 0.064 | 0.064 | 0.064 | 0.064 | — |
| Thymol | 0.062 | 0.062 | 0.062 | 0.062 | — |
| Eucalyptol | 0.089 | 0.089 | 0.089 | 0.089 | — |
| Poloxamer 407 | — | — | — | 0.2 | — |
| Arlasilk PTM[1] | — | — | — | — | — |
| ColaLipid C[2] | 2.0 | — | — | — | — |
| Cocamidopropyl betaine | — | 1.0 | — | — | — |
| Tween 20 | — | — | 2.0 | — | — |
| Sodium lauryl sulfate | — | — | — | 0.2 | — |
| Sorbitol (70% solution) | 10.0 | 10.0 | 10.0 | 10.0 | — |
| Sodium Benzoate | 0.077 | 0.077 | 0.077 | 0.077 | — |
| Flavor | 0.017 | 0.017 | 0.017 | 0.017 | — |
| Sweetner | 0.0706 | 0.0706 | 0.0706 | 0.0706 | — |
| FD&C Green #3 | 0.00004 | 0.00004 | 0.00004 | 0.00004 | — |
| Water | QS | QS | QS | QS | — |
| TOTAL | 100.0 | 100.0 | 100.0 | 100.0 | — |
| log RLU | 4.04 | 5.86 | 7.06 | 4.51 | 7.22 |
| M-factor | 3.18 | 1.36 | 0.16 | 2.71 | 0 |

[1]Myristamidopropyl PG-dimonium chloride phosphate, 40% in water (Croda Inc., Edison, NJ)
[2]Cocamidopropyl PG-dimonium chloride phosphate, 41% in water (Colonial Chemical, Inc., South Pittsburg, TN)

As shown by Table 3, each of inventive Examples J through O displayed still further improvement in biocidal activity (i.e., higher M-factor values), exhibiting M-factor values of 2.97 and above (i.e., log RLU values of 4.25 or below).

What is claimed is:

1. An oral composition, comprising:
   i. a phospholipid surfactant selected from the group consisting of cocamidopropyl PG-dimonium chloride phosphate, myristamidopropyl PG-dimonium chloride phosphate, and mixtures thereof, wherein the phospholipid surfactant is present in an amount of from about 0.01% to about 10% w/w of the total composition;
   ii. one or more water-insoluble noncationic bioactive agents selected from the group consisting of thymol, eucalyptol, menthol, methyl salicylate and mixtures thereof in a total amount of from about 0.16% to about 0.28% w/v of the total composition; and
   iii. at least one orally acceptable solvent comprising water.

2. The compositions according to claim 1 wherein one or more water-insoluble noncationic bioactive agents is a mixture of thymol, eucalyptol, menthol and methyl salicylate.

3. The composition of claim 2 wherein the phospholipid surfactant comprises myristamidopropyl PG-dimonium chloride phosphate.

4. The composition of claim 2 wherein the phospholipid surfactant comprises cocamidopropyl PG-dimonium chloride phosphate.

5. The compositions according to claim 1 further comprising an additional surfactant.

6. The compositions according to claim 5 wherein the additional surfactant is a nonionic surfactant.

7. The compositions according to claim 6 wherein the nonionic surfactant is a poly(oxyethylene)-poly(oxypropylene) block copolymer surfactant.

8. The composition according to claim 1 wherein the composition is essentially free of $C_2$-$C_4$ monohydric alcohols.

9. The composition according to claim 8 wherein the composition is free of $C_2$-$C_4$ monohydric alcohols.

10. The composition of claim 1 wherein the phospholipid surfactant comprises cocamidopropyl PG-dimonium chloride phosphate.

11. A method of treating plaque, gingivitis or gum disease, comprising the step of applying to the tissues of the oral cavity of a mammal in need of such treatment an amount of the composition of claim 1 effective to reduce symptoms associated with plaque, gingivitis or gum disease.

12. A method of treating or reducing symptoms associated with inflamed tissue, comprising the step of applying to the tissues of a mammal in need of such treatment an amount of the composition of claim 1 effective to reduce symptoms associated inflammation.

13. The composition of claim 1 wherein the phospholipid surfactant comprises myristamidopropyl PG-dimonium chloride phosphate.

* * * * *